US011872343B2

(12) United States Patent
Liaw et al.

(10) Patent No.: US 11,872,343 B2
(45) Date of Patent: Jan. 16, 2024

(54) VENTILATOR SYSTEM

(71) Applicants: Chen-Kun Liaw, Taipei (TW); Tai-Yin Wu, Taipei (TW); Yu-Ciao Liao, Taipei (TW); Yu-Yan Liao, Taipei (TW); Hsiang-Hung Liaw, Taipei (TW); Yu-Peng Liao, Taipei (TW); Yi-Hsuan Liao, Taipei (TW); Yen-Chun Liao, Taipei (TW); Chih-Ling Liao, Taipei (TW)

(72) Inventors: Chen-Kun Liaw, Taipei (TW); Tai-Yin Wu, Taipei (TW); Yu-Ciao Liao, Taipei (TW); Yu-Yan Liao, Taipei (TW); Hsiang-Hung Liaw, Taipei (TW); Yu-Peng Liao, Taipei (TW); Yi-Hsuan Liao, Taipei (TW); Yen-Chun Liao, Taipei (TW); Chih-Ling Liao, Taipei (TW)

( * ) Notice: Subject to any disclaimer, the term of this patent is extended or adjusted under 35 U.S.C. 154(b) by 390 days.

(21) Appl. No.: 17/213,254

(22) Filed: Mar. 26, 2021

(65) Prior Publication Data
US 2021/0299377 A1  Sep. 30, 2021

Related U.S. Application Data

(60) Provisional application No. 63/000,031, filed on Mar. 26, 2020.

(51) Int. Cl.
*A61M 16/00* (2006.01)
*A61M 16/06* (2006.01)
(Continued)

(52) U.S. Cl.
CPC ...... *A61M 16/024* (2017.08); *A61M 16/0057* (2013.01); *A61M 16/0063* (2014.02); *A61M 16/04* (2013.01); *A61M 16/06* (2013.01); *A61M 16/1005* (2014.02); *A61M 16/122* (2014.02); *A61M 16/202* (2014.02); *A61M 16/208* (2013.01); *A61M 2016/0027* (2013.01); *A61M 2202/0208* (2013.01);
(Continued)

(58) Field of Classification Search
CPC .............. A61M 16/00; A61M 16/0057; A61M 16/0063; A61M 16/0066; A61M 16/0078; A61M 16/022; A61M 16/024; A61M 16/0816; A61M 16/0875; A61M 16/122; A61M 16/202; A61M 2205/84; A61M 2202/0208; A61M 2016/0027; A62B 7/02; A62B 7/14; A62B 31/00; B64D 2231/02
See application file for complete search history.

(56) References Cited

U.S. PATENT DOCUMENTS

| | | | |
|---|---|---|---|
| 8,726,900 B1 * | 5/2014 | Nashed | A61M 16/0833 128/203.15 |
| 2009/0050151 A1 * | 2/2009 | Fuhrman | A61M 16/0084 128/205.12 |

(Continued)

*Primary Examiner* — Joseph D. Boecker

(57) ABSTRACT

A ventilator system includes a first air tank, a plurality of second air tanks communicated with the first air tank, a plurality of breathing devices respectively communicated with the second air tanks, a plurality of first vacuum tanks respectively communicated with the breathing devices, and a second vacuum tank communicated with the first vacuum tanks. The first air tank has a positive pressure relative to the second air tanks. The second vacuum tank has a negative pressure relative to the first vacuum tanks.

14 Claims, 2 Drawing Sheets

(51) Int. Cl.
*A61M 16/04* (2006.01)
*A61M 16/20* (2006.01)
*A61M 16/10* (2006.01)
*A61M 16/12* (2006.01)

(52) U.S. Cl.
CPC . *A61M 2205/3331* (2013.01); *A61M 2205/84* (2013.01); *A61M 2230/40* (2013.01)

(56) References Cited

U.S. PATENT DOCUMENTS

| | | | |
|---|---|---|---|
| 2009/0235932 A1* | 9/2009 | Nashed | A61M 16/0816 |
| | | | 128/203.29 |
| 2020/0398015 A1* | 12/2020 | Lum | A61M 16/0833 |
| 2021/0299388 A1* | 9/2021 | Vankoevering | A61M 16/20 |
| 2021/0346638 A1* | 11/2021 | Faulkner | A61M 16/024 |
| 2022/0031983 A1* | 2/2022 | Salehpoor | A61M 16/1005 |
| 2022/0370748 A1* | 11/2022 | Lehman | A61M 16/0858 |

* cited by examiner

VENTILATOR SYSTEM

FIELD OF THE INVENTION

The present invention relates to a ventilator system, and more particularly to a ventilator system for multiple clients.

BACKGROUND OF THE INVENTION

A ventilator can be used to help a patient who has respiratory distress. Conventionally, one ventilator is provided only for one patient. Therefore, the medical institutions may not have sufficient ventilators to save all patients when the number of patients having respiratory distress suddenly increases in an area.

Corona virus disease (officially called COVID-19) started since December 2019. Some patients would experience breathing difficulties due to the infiltrative injury to both lungs, which may be examined by X-ray. Some countries exclude the elderly patients from treatment due to insufficient respirator. Therefore, COVID-19 has caused a lot of death, and the number of deaths is stilling climbing.

Further, the medical staffs have to spend a lot of time to operate a ventilator connected to a patient in a closed ward. Therefore, the medical staffs may be infected in the ward.

In addition, the conventional ventilator is expensive. It is also difficult to manufacture a large number of ventilators quickly.

SUMMARY OF THE INVENTION

The present invention provides a ventilator system capable of providing to multiple patients at the same time. The ventilator system can be assembled quickly and inexpensively. With the ventilator system of the invention, the medical staffs may remotely supervise the patients instead of staying in a ward for a long time.

The present invention provides a ventilator system, which includes a first air tank, a plurality of second air tanks communicated with the first air tank, a plurality of breathing devices respectively communicated with the second air tanks, a plurality of first vacuum tanks respectively communicated with the breathing devices, and a second vacuum tank communicated with the first vacuum tanks. The first air tank has a positive pressure relative to the second air tanks. The second vacuum tank has a negative pressure relative to the first vacuum tanks.

In one embodiment of the present invention, the ventilator system further includes a plurality of one-way valves and a central control unit. The one-way valves are respectively connected between the first air tank and the second air tanks, between the second air tanks and the breathing devices, between the breathing devices and the first vacuum tanks, and between the second vacuum tank and the first vacuum tanks. The central control unit is electrically connected to the one-way valves to switch on or off the one-way valves, wherein each of the one-way valves is normally off.

In one embodiment of the present invention, the ventilator system further includes a plurality of pressure sensors respectively disposed in the first air tank, the second air tanks, the first vacuum tanks, the second vacuum tank and the breathing devices. The central control unit is electrically connected to the pressure sensors.

In one embodiment of the present invention, the ventilator system further includes at least one first air compressing unit and at least one a second air compressing unit. The at least one first air compressing unit is connected to the first air tank to supply compressed air into the first air tank. The at least one second air compressing unit is connected to the second vacuum tank to draw air from the second vacuum tank. The central control unit is electrically connected to the at least one first air compressing unit and the at least one second air compressing unit.

The ventilator system of the embodiments of the present invention can use one first air tank to provide compressed air for carrying oxygen gas to more than one patient at the same time. Therefore, more patients suffering from respiratory distress can be treated. In addition, the elements of the ventilator system, such as tanks, one-way valves and the air compressing units can be easily obtained and are inexpensive, thus, the ventilator system can be quickly assembled by the above elements. In addition, a medical staff may supervise and control more than one breathing conditions of the patients via the central control unit, instead of staying in a ward for a long time, therefore the risk of the medical staff being infected may be minimized.

In order to make the above and other objects, features and advantages of the present invention become more apparent and obvious, the preferred embodiments will be described in detail with reference to the accompanying drawings hereinafter.

BRIEF DESCRIPTION OF THE DRAWINGS

The present invention will become more readily apparent to those ordinarily skilled in the art after reviewing the following detailed description and accompanying drawings, in which.

DETAILED DESCRIPTION OF PREFERRED EMBODIMENTS

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1A:
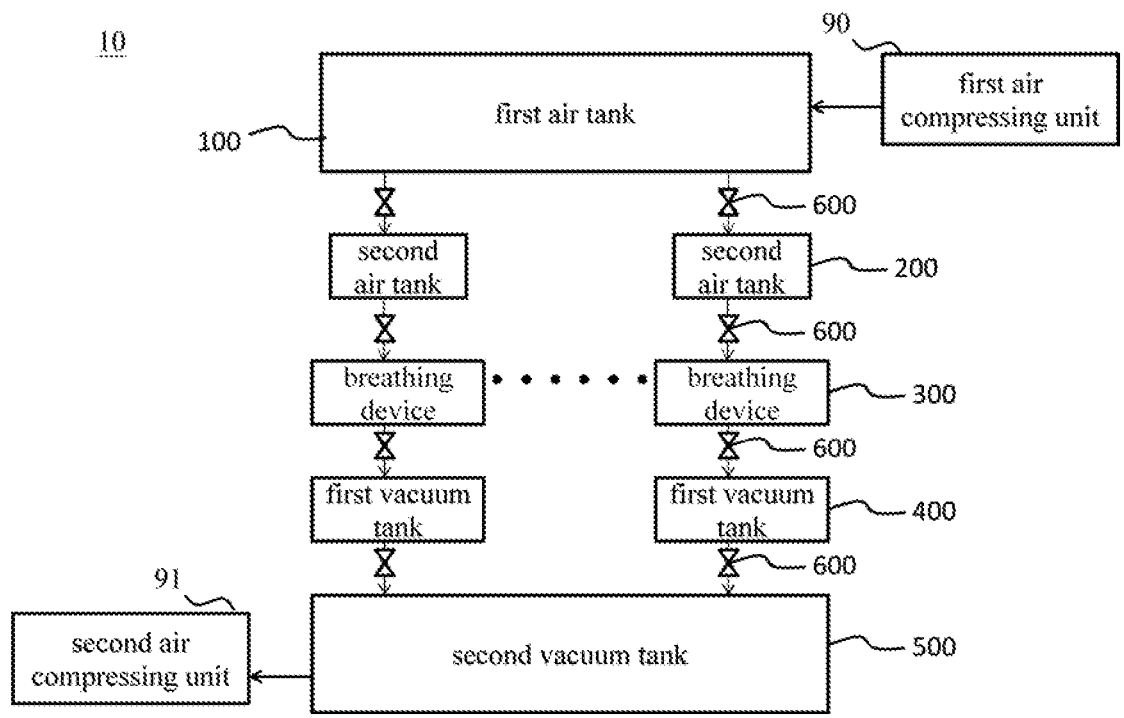
FIG. 1A is a schematic block diagram of a ventilator system of an embodiment of the present invention.
Figure 1B:
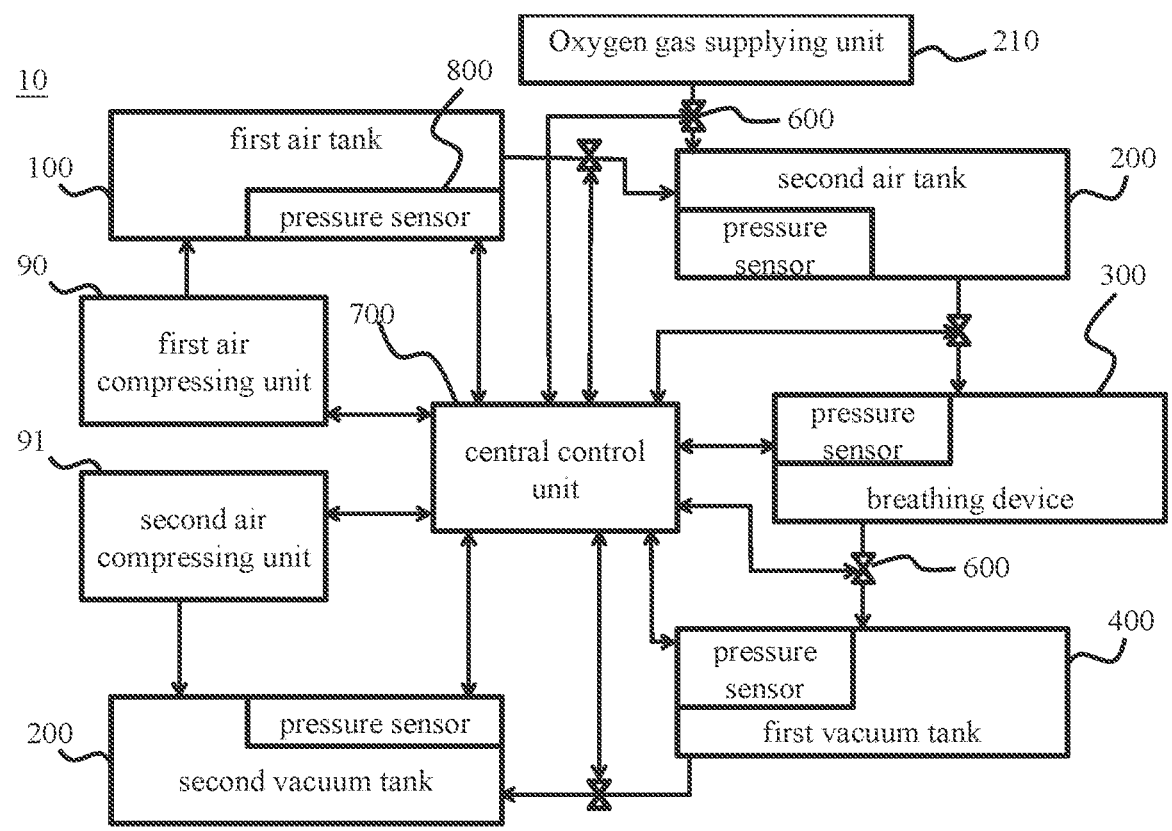
FIG. 1B is a schematic block diagram of a single unit of a ventilator system of an embodiment of the present invention.

FIG. 1A is a schematic block diagram of a ventilator system of an embodiment of the present invention. FIG. 1B is a schematic block diagram of a single unit of a ventilator system of an embodiment of the present invention. Referring to FIG. 1A and FIG. 1B, the ventilator system 10 of the embodiment includes a first air tank 100, a plurality of second air tanks 200, a plurality of breathing devices 300, a plurality of first vacuum tanks 400 and a second vacuum tank 500.

The second air tanks 200 are communicated with the first air tank 100. The breathing devices 300 are respectively communicated with the second air tanks 200. The first vacuum tanks 400 are respectively communicated with the breathing devices 300. The second vacuum tank 500 is communicated with the first vacuum tanks 400. The first air tank 100 has a positive pressure relative to the second air tanks 200. The second vacuum tank 500 has a negative pressure relative to the first vacuum tanks 400. Each of the breathing devices 300 can be connected to a lung of a patient.

In the embodiment, the ventilator system 10 further includes a plurality of one-way valves 600 and a central control unit 700. Some of the one-way valves 600 are respectively connected between the first air tank 100 and the second air tanks 200. Some of the one-way valves 600 are respectively connected between the second air tanks 200 and the breathing devices 300. Some of the one-way valves 600 are respectively connected between the breathing devices 300 and the first vacuum tanks 400. Some of the one-way valves 600 are respectively connected between the second vacuum tank 500 and the first vacuum tanks 400. The central control unit 700 is electrically connected to the one-way valves 600 to switch on or off the one-way valves 600. In the embodiment, each of the one-way valves 600 is normally off.

The central control unit 700 may be a computer or a server. The central control unit 700 may be electrically connected to the one-way valves 600 via wires, network cables, Wi-Fi or Bluetooth protocol, but is not limited thereto.

In the embodiment, the ventilator system 10 further includes a plurality of pressure sensors 800 respectively disposed in the first air tank 100, the second air tanks 200, the first vacuum tanks 400, the second vacuum tank 500 and the breathing devices 300. The central control unit 700 is electrically connected to the pressure sensors 800.

The first air tank 100 provides compressed air to the second air tanks 200. Each second air tank 200 may be further connected to an oxygen gas supplying unit 210, and therefore, the ventilator system 10 may include a plurality of oxygen gas supplying unit 210. The compressed air in each second air tank 200 may be mixed with the oxygen gas, and the mixed gas can be provided to a lung of a patient via the breathing device 300, wherein the breathing device 300 may be a mask or tracheal tube.

In order to help patients' breath, each of the second air tanks 200 has a target inspiration pressure P2, and each of the first vacuum tanks 400 has a target expiration pressure P6. The target inspiration pressure P2 and the target expiration pressure P6 can be variable depending on the individual patients.

Once the pressure sensor 800 detects that the pressure in the respective second air tank 200 is lower than P2, the central control unit 700 may switch on the respective one-way valve 600 between the first air tank 100 and the second air tank 200 and the respective one-way valve 600 between the oxygen gas supplying unit 210 and the second air tank 200 until the pressure in this second air tank 200 back to P2. It is assumed that a partial pressure of oxygen gas provided by the oxygen gas supplying unit 210 in each second air tank 200 is P3, and a partial pressure of air provided by the first air tank 100 in each second air tank 200 is P4, then P2=P3+P4.

Once the pressure sensor 800 detects that the pressure in the respective first vacuum tanks 400 is higher than P6, the central control unit 700 may switch on the respective one-way valve 600 between the respective first vacuum tank 400 and the second vacuum tank 500 until the pressure declines to P6.

When one of the breathing devices 300 is connected to a lung of a patient and the central control unit 700 confirms that the respective second air tank 200 has the target inspiration pressure P2 and the respective first vacuum tank 400 has the first target expiration pressure P6 via the respective pressure sensor 800, the central control unit 700 may switch on the one-way valve 600 between the respective second air tank 200 and this breathing device 300 for inspiration, and then switch on the one-way valve 600 between the respective first vacuum tank 200 and this breathing device 300 for expiration.

It is assumed that the volume of the respective second air tank 200 is V1, the tidal volume of the inspiration of the patient is V2, the instant air pressure after the inspiration of the respective second air tank 200 is P1, then the target inspiration pressure P2 of the respective second air tank 200 satisfies the following relationship: $P2=(V1+V2/V1)\times P1$. It is assumed that the volume of the respective first vacuum tank 400 is V3, the tidal volume of an expiration of the patient is V4, the instant air pressure after the expiration of the respective first vacuum tank 400 is P5, then the target expiration pressure P6 of the respective first vacuum tank 400 satisfies the following relationship: $P6=(V3-V4/V3)\times P5$.

The central control unit 700 may switch on the one-way valve 600 between the first air tank 100 and the second air tank 200 and the one-way valve 600 between the oxygen gas supplying unit 210 and the second air tank 200 after an inspiration. To maintain a desired oxygen concentration in the second air tank 200, the central control unit 700 may calculate the required air amount and the required oxygen gas amount based on the tidal volume and a predetermined oxygen gas partial pressure. For example, the central control unit 700 may switch on the one-way valve 600 between the oxygen gas supplying unit 210 and the second air tank 200 first to meet the required oxygen gas amount, and then switch on the one-way valve 600 between the first air tank 100 and the second air tank 200 to meet the target inspiration pressure P2.

Similarly, the central control unit 700 may switch on the one-way valve 600 between the first vacuum tank 400 and the second vacuum tank 500 after expiration.

In the embodiment, the ventilator system 10 further includes at least one first air compressing unit 90 and at least one a second air compressing unit 91. The first air compressing unit 90 is connected to the first air tank 100 to supply compressed air into the first air tank 100. The second air compressing unit 91 is connected to the second vacuum tank 200 to draw air from the second vacuum tank 200. The central control unit 91 is electrically connected to the first air compressing unit 90 and the second air compressing unit 91. FIG. 1A and FIG. 1B illustrates one first air compressing unit 90 and one second air compressing unit 91, but the invention does not limit the numbers of the first air compressing units 90 and the second air compressing units 91.

The central control unit 700 may activate the first air compressing unit 90 when the pressure sensor 800 detects that the air pressure of the first air tank 100 is smaller than a predetermined lowest pressure. The central control unit 700 may activate the second air compressing unit 91 when the pressure sensor 800 detects that the air pressure of the second vacuum tank 500 is higher than a predetermined highest pressure.

The ventilator system 10 further includes disinfectors (not shown) respectively disposed in the first air tank 100 and the second vacuum tank 500 to kill the virus from patients.

The ventilator system of the embodiments of the present invention can use one first air tank to provide compressed air for carrying oxygen gas to more than one patient at the same time. Therefore, more patients suffering from respiratory distress can be treated. In addition, the elements of the ventilator system, such as tanks, one-way valves and the air compressing units can be easily obtained and are inexpensive, thus, the ventilator system can be quickly assembled by the above elements. In addition, a medical staff may supervise and control more than one breathing conditions of the patients via the central control unit, instead of staying in a ward for a long time, therefore the risk of the medical staff being infected may be minimized.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A ventilator system, comprising:
   a first air tank;
   a plurality of second air tanks, communicated with the first air tank;
   a plurality of breathing devices, respectively communicated with the second air tanks;
   a plurality of first vacuum tanks, respectively communicated with the breathing devices; and
   a second vacuum tank, communicated with the first vacuum tanks,
   wherein the first air tank has a positive pressure relative to the second air tanks,
   wherein the second vacuum tank has a negative pressure relative to the first vacuum tanks.

2. The ventilator system according to claim 1, further comprising:
   a plurality of one-way valves, respectively connected between the first air tank and the second air tanks, between the second air tanks and the breathing devices, between the breathing devices and the first vacuum tanks, and between the second vacuum tank and the first vacuum tanks.

3. The ventilator system according to claim 1, further comprising:
   a first air compressing unit, connected to the first air tank, wherein the first air compressing unit is configured to supply compressed air into the first air tank; and
   a second air compressing unit, connected to the second vacuum tank, wherein the second air compressing unit is configured to draw air from the second vacuum tank.

4. The ventilator system according to claim 1, further comprising a plurality of oxygen gas supplying units and a plurality of one-way valves, wherein the oxygen gas supplying units are respectively communicated to the second air tanks to supply oxygen gas into the second air tanks, and the one-way valves are respectively connected between the oxygen gas supplying units and the second air tanks.

5. The ventilator system according to claim 1, further comprising a plurality of pressure sensors respectively disposed in the first air tank, the second air tanks, the first vacuum tanks, the second vacuum tank and the breathing devices.

6. The ventilator system according to claim 1, wherein each of the breathing devices comprises a mask or a tracheal tube.

7. A ventilator system, comprising:
   a first air tank;
   a plurality of second air tanks, communicated with the first air tank;
   a plurality of breathing devices, respectively communicated with the second air tanks;
   a plurality of first vacuum tanks, respectively communicated with the breathing devices;
   a second vacuum tank, communicated with the first vacuum tanks;
   a plurality of one-way valves, respectively connected between the first air tank and the second air tanks, between the second air tanks and the breathing devices, between the breathing devices and the first vacuum tanks, and between the second vacuum tank and the first vacuum tanks: and
   a central control unit, electrically connected to the one-way valves to switch on or off the one-way valves, wherein each of the one-way valves is normally off,
   wherein the first air tank has a positive pressure relative to the second air tanks,
   wherein the second vacuum tank has a negative pressure relative to the first vacuum tanks.

8. The ventilator system according to claim 7, further comprising:
   a plurality of pressure sensors, respectively disposed in the first air tank, the second air tanks, the first vacuum tanks, the second vacuum tank and the breathing devices,
   wherein the central control unit is electrically connected to the pressure sensors.

9. The ventilator system according to claim 8, wherein one of the breathing devices is configured to be connected to a lung of a patient, a volume of the respective second air tank is $V1$, a tidal volume of a latest inspiration of the patient is $V2$, an instant air pressure after the latest inspiration of the respective second air tank is $P1$, a target inspiration pressure of the respective second air tank for inspiration of the patient is $P2$, and $P2=(V1+V2/V1)\times P1$.

10. The ventilator system according to claim 9, further comprising a plurality of oxygen gas supplying units respectively communicated to the second air tanks to supply oxygen gas into the second air tanks, wherein a partial pressure of the oxygen gas provided by one of the oxygen gas supplying units in the respective second air tank is $P3$, and a partial pressure of air provided by the first air tank in the respective second air tank is $P4$, and $P2=P3+P4$.

11. The ventilator system according to claim 8, wherein one of the breathing devices is configured to be connected to a lung of a patient, a volume of the respective first vacuum tank is $V3$, a tidal volume of a latest expiration of the patient is $V4$, an instant air pressure after the latest expiration of the first vacuum tank is $P5$, a target expiration pressure of the respective first vacuum tank for expiration of the patient is $P6$, and $P6=(V3-V4/V3)\times P5$.

12. The ventilator system according to claim 8, further comprising:
   at least one first air corn pressing unit, connected to the first air tank, wherein the at least one first air compressing unit is configured to supply compressed air into the first air tank; and
   at least one second air compressing unit, connected to the second vacuum tank, wherein the at least one second air compressing unit is configured to draw air from the second vacuum tank,
   wherein the central control unit is electrically connected to the at least one first air compressing unit and the at least one second air compressing unit.

13. The ventilator system according to claim 12, wherein the central control unit is configured to activate the at least one first air compressing unit when an air pressure of the first air tank is lower than a predetermined lowest pressure.

14. The ventilator system according to claim 12, wherein the central control unit is configured to activate the at least one second air compressing unit when an air pressure of the second vacuum tank is higher than a predetermined highest pressure.

* * * * *